(12) United States Patent
Kobayashi et al.

(10) Patent No.: US 10,561,366 B2
(45) Date of Patent: Feb. 18, 2020

(54) MEASURING SYSTEM AND METHOD FOR EVALUATING CONDITION OF PATIENT

(71) Applicant: NIHON KOHDEN CORPORATION, Tokyo (JP)

(72) Inventors: Naoki Kobayashi, Tokyo (JP); Hideaki Hirabara, Tokyo (JP); Katsuyuki Horie, Tokyo (JP); Katsuhide Tone, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1095 days.

(21) Appl. No.: 14/928,448

(22) Filed: Oct. 30, 2015

(65) Prior Publication Data

US 2016/0128634 A1    May 12, 2016

(30) Foreign Application Priority Data

Nov. 11, 2014   (JP) .................................. 2014-228550

(51) Int. Cl.
*A61B 5/1455* (2006.01)
*A61B 5/026* (2006.01)
*A61B 5/00* (2006.01)

(52) U.S. Cl.
CPC .......... *A61B 5/6843* (2013.01); *A61B 5/0053* (2013.01); *A61B 5/0261* (2013.01);
(Continued)

(58) Field of Classification Search
CPC .............. A61B 5/1455; A61B 5/14551; A61B 5/14552; A61B 5/6814; A61B 5/6825;
(Continued)

(56) References Cited

U.S. PATENT DOCUMENTS 5,050,613 A    9/1991  Newman et al.
6,334,065 B1 * 12/2001  Al-Ali ................ A61B 5/14551
                                                 600/323
(Continued)

FOREIGN PATENT DOCUMENTS

JP   H11-089808 A   4/1999
JP   2003-235818 A  8/2003
(Continued)

OTHER PUBLICATIONS

Extended European Search Report issued in European Patent Application No. EP 15 19 2715 dated Aug. 30, 2016.
(Continued)

*Primary Examiner* — Eric F Winakur
(74) *Attorney, Agent, or Firm* — Pearne & Gordon LLP

(57)    ABSTRACT

A measuring system includes a first sensor, a second sensor, a first measurement value calculator that, based on a change of an amount of received light that is measured by the first sensor, calculates a first measurement value indicating an index related to a blood oxygen saturation or a blood refill time, a second measurement value calculator that, based on a change of an amount of received light that is measured by the second sensor, calculates a second measurement value indicating an index related to a blood oxygen saturation or a blood refill time, and a pressure controller that controls the first sensor and the second sensor so that a time difference between a start of compression release by the first sensor and a start of compression release by the second sensor is within a predetermined time period.

20 Claims, 12 Drawing Sheets

(52) U.S. Cl.
CPC ........ *A61B 5/14552* (2013.01); *A61B 5/6814* (2013.01); *A61B 5/6826* (2013.01); *A61B 5/7246* (2013.01); *A61B 5/7282* (2013.01); *A61B 5/14551* (2013.01); *A61B 2505/01* (2013.01)

(58) Field of Classification Search
CPC ... A61B 5/6826; A61B 5/6843; A61B 5/0261; A61B 5/7246; A61B 5/7282
See application file for complete search history.

(56) References Cited

U.S. PATENT DOCUMENTS

| | | |
|---|---|---|
| 2003/0158488 A1 | 8/2003 | Narimatsu et al. |
| 2003/0236452 A1 | 12/2003 | Melker et al. |
| 2004/0230108 A1 | 11/2004 | Melker et al. |
| 2004/0260161 A1 | 12/2004 | Melker et al. |
| 2006/0173258 A1 | 8/2006 | Kobayashi et al. |
| 2007/0027375 A1 | 2/2007 | Melker et al. |
| 2007/0282182 A1 | 12/2007 | Messerges et al. |
| 2008/0058621 A1 | 3/2008 | Melker et al. |
| 2010/0192952 A1 | 8/2010 | Melker et al. |
| 2011/0066034 A1 | 3/2011 | Rensen et al. |
| 2012/0078069 A1 | 3/2012 | Melker |
| 2012/0130211 A1 | 5/2012 | Kobayashi et al. |
| 2014/0094670 A1 | 4/2014 | Melker |
| 2014/0114152 A1 | 4/2014 | Fournier |
| 2014/0155704 A1 | 6/2014 | Melker et al. |
| 2014/0155713 A1 | 6/2014 | Melker et al. |
| 2014/0158132 A1 | 6/2014 | Melker |
| 2014/0180026 A1 | 6/2014 | Melker |
| 2014/0213865 A1 | 7/2014 | Kobayashi et al. |
| 2014/0213884 A1 | 7/2014 | Hirabara et al. |
| 2014/0243630 A1 | 8/2014 | Melker et al. |
| 2014/0243631 A1 | 8/2014 | Melker |
| 2016/0128634 A1 | 5/2016 | Kobayashi et al. |
| 2017/0238871 A1 | 8/2017 | Melker |
| 2018/0008155 A1 | 1/2018 | Melker et al. |
| 2018/0049654 A1 | 2/2018 | Melker et al. |

FOREIGN PATENT DOCUMENTS

| | | |
|---|---|---|
| JP | 2005-529713 A | 10/2005 |
| JP | 2006-231012 A | 9/2006 |
| JP | 2011-520581 A | 7/2011 |
| JP | 2012-115640 A | 6/2012 |
| JP | 2014-147473 A | 8/2014 |
| JP | 2014-147474 A | 8/2014 |
| JP | 2016-087326 A | 5/2016 |
| WO | 2014-138275 A1 | 9/2014 |

OTHER PUBLICATIONS

Japanese Office action issued in Patent Application No. JP 2014-228550 dated Apr. 19, 2018.
Japanese Office Action issued in Patent Application No. JP-2014-228550 dated Sep. 26, 2017.
Partial European Search Report for Application No. 15192715.9-1657 dated Apr. 7, 2016.
Japanese Office Action issued in Japanese Patent Application No. 2018-117543 dated Apr. 24, 2019.

* cited by examiner

FIG. 5

| FINGERTIP / FOREHEAD | SECOND MEASUREMENT VALUE < Tth1 | SECOND MEASUREMENT VALUE ≧ Tth1 |
|---|---|---|
| FIRST MEASUREMENT VALUE < Tth1 | Case 1 | Case 3 |
| FIRST MEASUREMENT VALUE ≧ Tth1 | Case 2 | Case 4 |

FIG. 6

| FINGERTIP (LEFT) \ FINGERTIP (RIGHT) | SECOND MEASUREMENT VALUE < Tth1 | SECOND MEASUREMENT VALUE ≧ Tth1 |
|---|---|---|
| FIRST MEASUREMENT VALUE < Tth1 | Case 5 | Case 7 |
| FIRST MEASUREMENT VALUE ≧ Tth1 | Case 6 | Case 8 |

FIG. 7

FIRST MEASUREMENT VALUE = FINGERTIP
SECOND MEASUREMENT VALUE = FOREHEAD

| | |
|---|---|
| FIRST MEASUREMENT VALUE - SECOND MEASUREMENT VALUE > Tth2 | Case 9 |
| SECOND MEASUREMENT VALUE - FIRST MEASUREMENT VALUE > Tth2 | Case 10 |
| OTHERS | Case 11 |

FIG. 8

FIRST MEASUREMENT VALUE = FINGERTIP OF LEFT HAND
SECOND MEASUREMENT VALUE = FINGERTIP OF RIGHT HAND

| | |
|---|---|
| FIRST MEASUREMENT VALUE - SECOND MEASUREMENT VALUE > Tth2 | Case 12 |
| SECOND MEASUREMENT VALUE - FIRST MEASUREMENT VALUE > Tth2 | Case 13 |
| OTHERS | Case 14 |

FIG. 9

FIRST MEASUREMENT VALUE = FINGERTIP
SECOND MEASUREMENT VALUE = FOREHEAD

| | | | |
|---|---|---|---|
| FIRST MEASUREMENT VALUE < Tth1 | SECOND MEASUREMENT VALUE < Tth1 | FIRST MEASUREMENT VALUE - SECOND MEASUREMENT VALUE > Tth2 | Case 15 |
| | | SECOND MEASUREMENT VALUE - FIRST MEASUREMENT VALUE > Tth2 | Case 16 |
| | | OTHERS | Case 17 |
| | SECOND MEASUREMENT VALUE ≧ Tth1 | FIRST MEASUREMENT VALUE - SECOND MEASUREMENT VALUE > Tth2 | Case 18 |
| | | SECOND MEASUREMENT VALUE - FIRST MEASUREMENT VALUE > Tth2 | Case 19 |
| | | OTHERS | Case 20 |
| FIRST MEASUREMENT VALUE ≧ Tth1 | SECOND MEASUREMENT VALUE < Tth1 | FIRST MEASUREMENT VALUE - SECOND MEASUREMENT VALUE > Tth2 | Case 21 |
| | | SECOND MEASUREMENT VALUE - FIRST MEASUREMENT VALUE > Tth2 | Case 22 |
| | | OTHERS | Case 23 |
| | SECOND MEASUREMENT VALUE ≧ Tth1 | FIRST MEASUREMENT VALUE - SECOND MEASUREMENT VALUE > Tth2 | Case 24 |
| | | SECOND MEASUREMENT VALUE - FIRST MEASUREMENT VALUE > Tth2 | Case 25 |
| | | OTHERS | Case 26 |

FIG. 10

FIRST MEASUREMENT VALUE = FINGERTIP OF LEFT HAND
SECOND MEASUREMENT VALUE = FINGERTIP OF RIGHT HAND

| | | | |
|---|---|---|---|
| FIRST MEASUREMENT VALUE < Tth1 | SECOND MEASUREMENT VALUE < Tth1 | FIRST MEASUREMENT VALUE - SECOND MEASUREMENT VALUE > Tth2 | Case 27 |
| | | SECOND MEASUREMENT VALUE - FIRST MEASUREMENT VALUE > Tth2 | Case 28 |
| | | OTHERS | Case 29 |
| | SECOND MEASUREMENT VALUE ≥ Tth1 | FIRST MEASUREMENT VALUE - SECOND MEASUREMENT VALUE > Tth2 | Case 30 |
| | | SECOND MEASUREMENT VALUE - FIRST MEASUREMENT VALUE > Tth2 | Case 31 |
| | | OTHERS | Case 32 |
| FIRST MEASUREMENT VALUE ≥ Tth1 | SECOND MEASUREMENT VALUE < Tth1 | FIRST MEASUREMENT VALUE - SECOND MEASUREMENT VALUE > Tth2 | Case 33 |
| | | SECOND MEASUREMENT VALUE - FIRST MEASUREMENT VALUE > Tth2 | Case 34 |
| | | OTHERS | Case 35 |
| | SECOND MEASUREMENT VALUE ≥ Tth1 | FIRST MEASUREMENT VALUE - SECOND MEASUREMENT VALUE > Tth2 | Case 36 |
| | | SECOND MEASUREMENT VALUE - FIRST MEASUREMENT VALUE > Tth2 | Case 37 |
| | | OTHERS | Case 38 |

MEASURING SYSTEM AND METHOD FOR EVALUATING CONDITION OF PATIENT

CROSS REFERENCE TO RELATED APPLICATION

This application is based on Japanese Patent Applications No. 2014-228550 filed on Nov. 11, 2014, the contents of which are incorporated herein by reference.

BACKGROUND

The present invention relates to a measuring system and a method for evaluating the condition of a patient.

The blood refill time is one of indexes for knowing the tissue perfusion of the subject. The blood refill time is handled as a simple index for evaluating whether shock occurs or not. The blood refill time is widely used in the field of emergency medicine in order to determine necessity/unnecessity of transfusion, triage category (evaluation of the priority in the case where many persons are injured or sickened), or the like. Also with respect to the degree of oxygenation of blood (arterial oxygen saturation), the blood refill time is important to determine whether blood is sufficiently supplied to the living tissue or not.

In usual measurement of the blood refill time, a medical person compresses the living tissue of the subject, such as a finger nail, and, after the compression is released, visually checks the color change of the nail or the skin. When the color returns to the original one within approximately two seconds, it is determined that the subject is in the normal condition. In the technique, however, the living tissue is manually compressed, and the change of the skin color is visually checked. Therefore, the technique has poor quantitative performance, and a measurement error easily occurs.

Therefore, a technique in which the blood refill time is measured by using a mechanism similar to a pulse oximeter has been proposed (JP-A-2012-115640). In the technique, light of a wavelength which can be absorbed by blood enters living tissue (mainly, the fingertip), and the intensity of light which transmits through the living tissue is measured by an optical sensor. In this case, when the living tissue is compressed by using an actuator, blood is evacuated from the living tissue of the compressed portion, and hence the intensity of the transmitted light is increased.

When the compression is released, the living tissue of the portion is filled with blood, and therefore the intensity of the transmitted light is decreased. The blood refill time is identified based on the time period which elapses after the release of the compression until the transmitted light intensity returns to the original level.

It is known that the blood flow in the vicinity of the fingertip is largely affected by the temperature and the activity of the nervous system. By contrast, the blood flow in the vicinity of the forehead is less affected by the temperature and the activity of the nervous system. Also with respect to a measurement of the percutaneous arterial oxygen saturation (SpO2) using a pulse oximeter, it is known that it cannot be measured in the fingertip because the peripheral circulation is poor, but, in the forehead, the measurement is highly possible.

Also in a measurement of the blood refill time, a waveform which is measured in the vicinity of the fingertip is affected by both the peripheral circulation and the central circulation. Even in the above-described technique in which the measurement is performed based on the detection of transmitted light, therefore, the value of the blood refill time which is measured in the vicinity of the fingertip is sometimes different from that which is measured in the vicinity of the forehead.

In the case where the subject suffers arteriosclerosis obliterans (ASO), moreover, the value of the blood refill time which is measured in the fingertip of one of the hands is sometimes different from that which is measured in the fingertip of the other hand. That is, the blood refill time that is measured in the hand in which the obstruction in a blood vessel progresses has a larger value.

As described above, a measurement value of the blood refill time is affected by various factors. Therefore, there arises a problem in that, when the blood refill time is measured in one body portion of the subject, it is impossible to correctly determine the condition of the cardiovascular system of the subject.

A similar problem arises in a measurement of an index related to the blood oxygen saturation. That is, also a measurement value of an index related to the blood oxygen saturation may be varied depending on the measurement location. Therefore, there is a possibility that, when the blood oxygen saturation is measured in on one body portion of the subject, it is impossible to correctly determine the condition of the cardiovascular system of the subject.

In a measurement of the blood refill time or an index related to the blood oxygen saturation which is performed only in a certain body portion of the subject, namely, there is a problem in that the condition of the cardiovascular system of the subject cannot be correctly determined.

The invention has been conducted in view of the above-discussed problem. It is a main object of the invention to provide a measuring system, measuring apparatus, and method for evaluating the condition of a patient in which the condition of the cardiovascular system of the subject can be correctly determined.

SUMMARY

According to an aspect of the invention, a measuring system includes a first sensor that emits light to a first portion of a subject, compresses the first portion, and measures reflected light or transmitted light from the first portion, a second sensor that emits light to a second portion of the subject, compresses the second portion, and measures reflected light or transmitted light from the second portion, a first measurement value calculator that, based on a change of an amount of received light that is measured by the first sensor, calculates a first measurement value indicating an index related to a blood oxygen saturation or a blood refill time, a second measurement value calculator that, based on a change of an amount of received light that is measured by the second sensor, calculates a second measurement value indicating an index related to a blood oxygen saturation or a blood refill time, and a pressure controller that controls the first sensor and the second sensor so that a time difference between a start of compression release by the first sensor and a start of compression release by the second sensor is within a predetermined time period.

BRIEF DESCRIPTION OF DRAWINGS

FIG. 5 is a view showing an evaluation method performed by an evaluator 214 in Embodiment 2.

FIG. 6 is a view showing the evaluation method performed by the evaluator 214 in Embodiment 2.

FIG. 7 is a view showing an evaluation method performed by the evaluator 214 in Embodiment 2.

FIG. 8 is a view showing an evaluation method performed by the evaluator 214 in Embodiment 2.

FIG. 9 is a view showing an evaluation method performed by the evaluator 214 in Embodiment 2.

FIG. 10 is a view showing an evaluation method performed by the evaluator 214 in Embodiment 2.

DETAILED DESCRIPTION OF EMBODIMENTS

<Embodiment 1>

Figure 1:
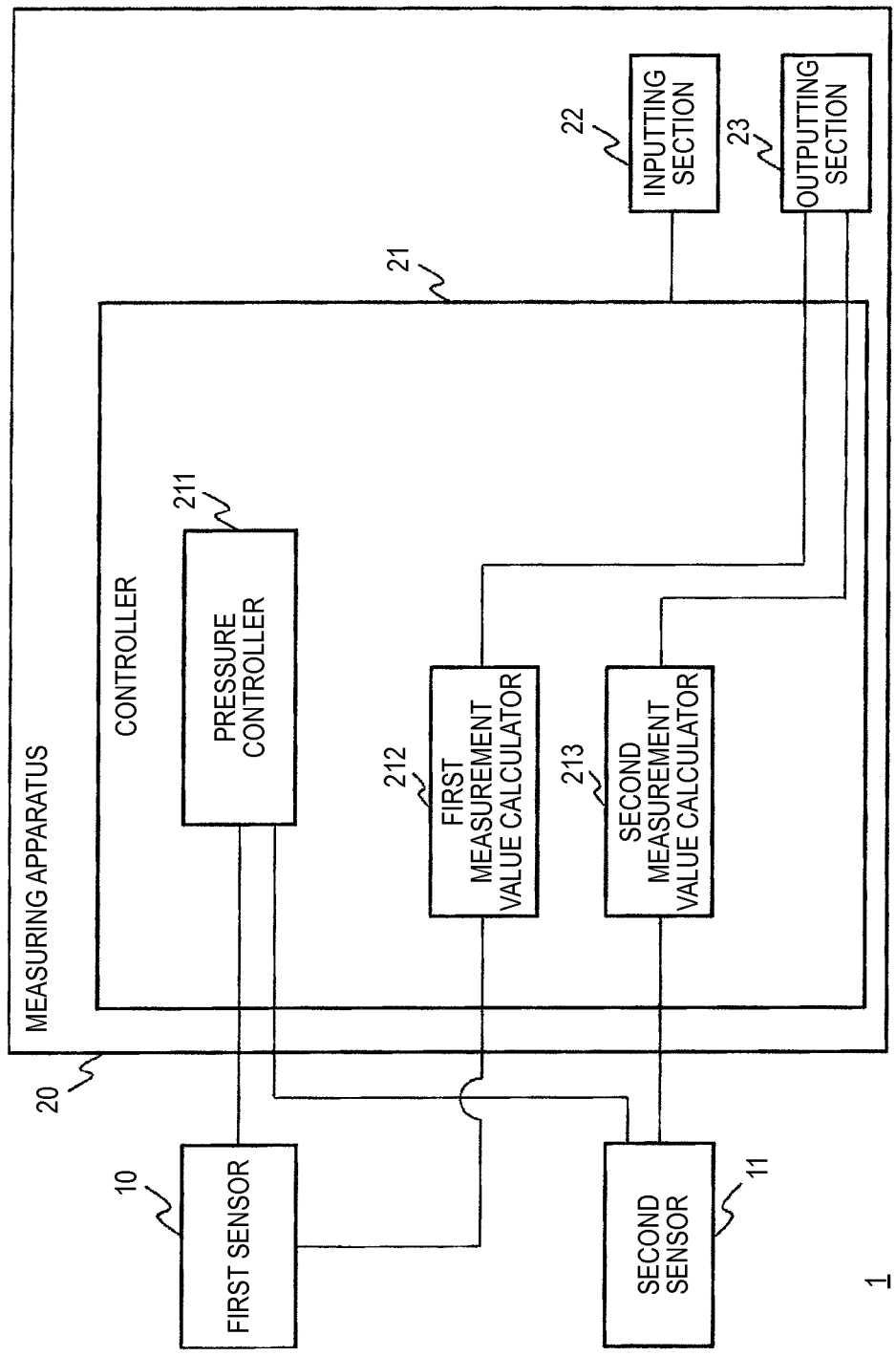
FIG. 1 is a block diagram showing the configuration of a measuring system 1 of Embodiment 1.

Hereinafter, an embodiment of the invention will be described with reference to the drawings. FIG. 1 is a block diagram showing the configuration of a measuring system 1 of the embodiment. The measuring system 1 includes a first sensor 10, a second sensor 11, and a measuring apparatus 20.

The first sensor 10 is used for measuring the blood refill time or index related to the blood oxygen saturation of the subject. In any one of the measurements, the first sensor 10 compresses the living tissue in accordance with the control of the measuring apparatus 20, emits light to the living tissue, and measures reflected light or transmitted light (hereinafter, referred to as "reflected/transmitted light") from the living tissue. In the case where an index related to the blood oxygen saturation is to be measured, the first sensor 10 emits light of a plurality of wavelengths (first light having a first wavelength λ1, and second light having a second wavelength λ2) to the living tissue. The first sensor 10 internally has a device such as a photodiode to perform the above-described light emission process. For example, the first sensor 10 has a bag body, and, when air is introduced into the bag body, the living tissue of the subject is compressed.

Similarly with the first sensor 10, the second sensor 11 is used for measuring the blood refill time or index related to the blood oxygen saturation of the subject. The second sensor 11 may be configured equivalently to the first sensor 10. The first sensor 10 and the second sensor 11 are attached to different places (for example, the finger of the left hand and that of the right hand) of the subject, respectively. Hereinafter, the place where the first sensor 10 is attached is referred to as the first portion, and the place where the second sensor 11 is attached is referred to as the second portion.

The first sensor 10 and the second sensor 11 may have an adequate shape according to the place where the sensor is to be attached. In the case where the first and second sensors 10, 11 are to be attached to the fingertips, the sensors may have a probe-like shape similarly with the case of a usual SpO2 measurement. In the case where the first and second sensors 10, 11 are to be attached to the forehead or the like, the sensors may be of the type in which each of the sensors is bonded to the subject through a seal-like adhesive member.

Each of the first and second sensors 10, 11 measures the amount of the reflected/transmitted light received from the living tissue, and notifies the measuring apparatus 20 of the measured amount of received light.

The measuring apparatus 20 includes a controller 21, an inputting section 22, and an outputting section 23. The controller 21 controls the measuring apparatus 20 and various sensors (the first sensor 10 and the second sensor 11), and includes a pressure controller 211, a first measurement value calculator 212, and a second measurement value calculator 213.

The pressure controller 211 controls the strengths of compressions which are applied by the first and second sensors 10, 11 to the living tissue of the subject. Specifically, the pressure controller 211 controls the amounts of the air inflows into the air bags to control the strengths of compressions which are applied by the first and second sensors 10, 11 to the living tissue of the subject.

The pressure controller 211 controls the timing of starting the release of compression in the first sensor 10, and that of starting the release of compression in the second sensor 11 so that the timings are substantially simultaneous. When the compression releases of the first and second portions are started substantially simultaneously, the blood refills in the both portions are started at the same timing.

Preferably, the pressure controller 211 controls compressions so that the time period from the start of the compression release by the first sensor 10 to the end of the compression is substantially equal to that from the start of the compression release by the second sensor 11 to the end of the compression. In this case, the conditions of the compressions on the first and second portions are substantially identical with each other, and therefore more correct measurement values (first and second measurement values which will be described later) can be obtained.

The first measurement value calculator 212 calculates to the blood refill time or index related to the blood oxygen saturation based on the amount of received light measured by the first sensor 10. An example of the method of calculating the blood refill time, and that of the method of measuring an index related to the blood oxygen saturation are described in detail in JP-A-2014-147474 and JP-A-2014-147473 which are publications of the patent applications of the same inventors as those of the present invention. Therefore, a detailed description of the methods of calculating the blood refill time and an index related to the blood oxygen saturation will be omitted, and summaries of the calculation methods will be briefly described.

Figure 2:
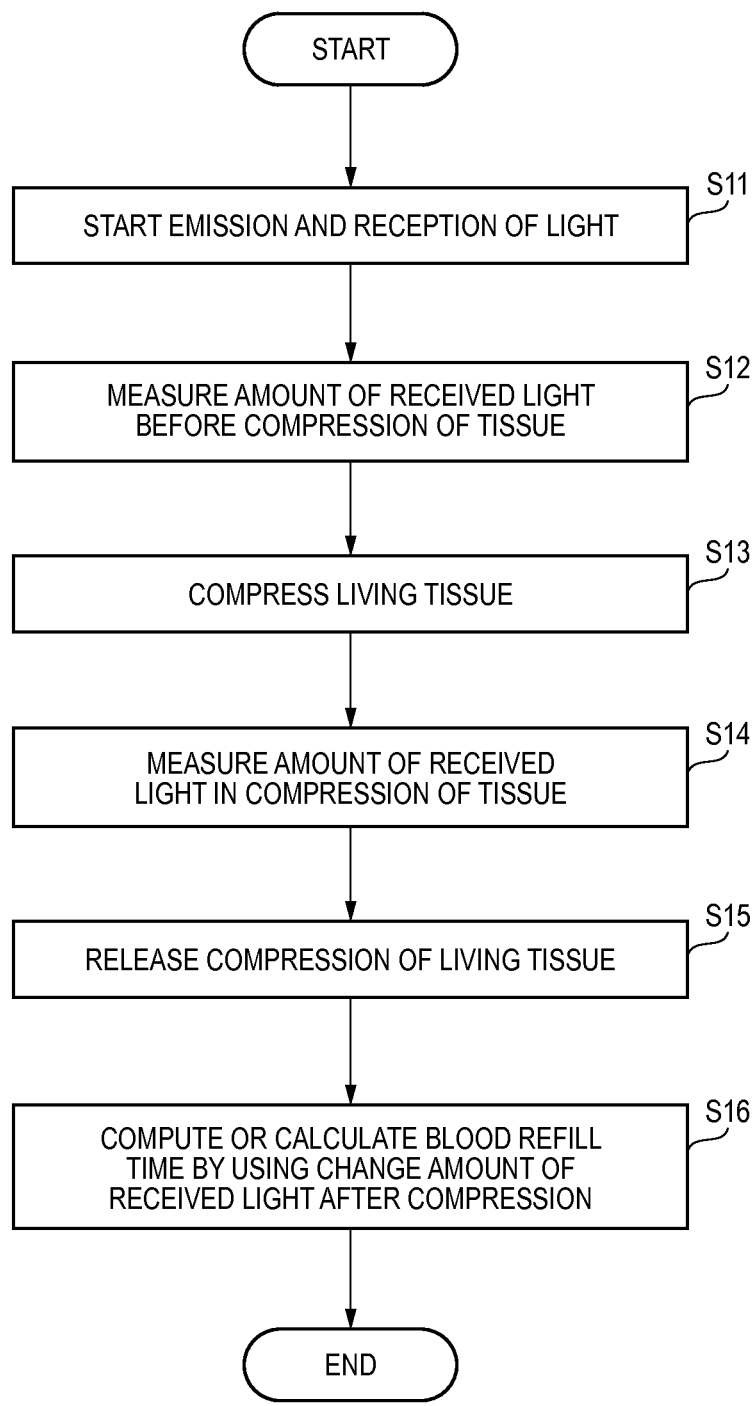
FIG. 2 is a flowchart showing the flow of a process of calculating the blood refill time in Embodiment 1.

First, a summary of the method of calculating the blood refill time will be described with reference to FIG. 2. The controller 21 starts light emission and light reception of the first sensor 10 at a predetermined timing (for example, every 30 minutes) (S11). In this step, the pressure controller 211 controls compression on the living tissue so as not to compress the living tissue. The first measurement value calculator 212 measures the amount of received light before compression on the living tissue, from the first sensor 10 (S12). After acquisition of the amount of received light before compression, the pressure controller 211 starts compression on the living tissue (S13). The first measurement value calculator 212 measures the amount of received light in the state of compression on the living tissue, from the first sensor 10 (S14). After compression is sufficiently performed, the pressure controller 211 releases the compression on the living tissue (S15). The first measurement value calculator 212 computes or calculates the time period which is elapsed from the timing when the compression on the living tissue is released, to the timing when the amount of received light attenuates to a value that is approximately equal to the amount of received light before the compression, as the blood refill time (S16).

The above is a summary of the method of calculating the blood refill time. Then, a summary of the method of calculating an index related to the blood oxygen saturation will be described.

The first measurement value calculator 212 acquires, from the first sensor 10, a first signal S1 corresponding to the received light intensity of first light (first wavelength λ1), and a second signal S2 corresponding to the received light intensity of second light (second wavelength λ2). The first measurement value calculator 212 acquires a first light attenuation A1 based on the first signal S1, and a second light attenuation A2 based on the second signal S2. Then, the first measurement value calculator 212 acquires a blood-derived light attenuation Ab based on the light attenuations A1 and A2. The first measurement value calculator 212 acquires information ΔAb related to the blood oxygen saturation based on the change amount of the light attenuation Ab, or, in the case where light of three or more wavelengths is used, acquires the blood oxygen saturation S. In the specification, it is assumed that "index related to the blood oxygen saturation" is a concept including the above described information ΔAb or the blood oxygen saturation S. Moreover, "index related to the blood oxygen saturation" may be another index other than the information ΔAb and the blood oxygen saturation S, as far as the other index is calculated from the amount of received light which is obtained by compressing the living body and emitting light of a plurality of wavelengths, and related to the blood oxygen saturation.

The above is a summary of the method of calculating an index related to the blood oxygen saturation. In accordance with an operation (operation by the medical person) through the inputting section 22, the first measurement value calculator 212 can measure one of the blood refill time and an index related to the blood oxygen saturation.

Based on the amount of received light measured by the second sensor 11 attached to the second portion, the second measurement value calculator 213 calculates the blood refill time or index related to the blood oxygen saturation of the second portion. The measurement technique is similar to that of the first measurement value calculator 212.

Hereinafter, the blood refill time or index related to the blood oxygen saturation measured by the first measurement value calculator 212 is referred to also as "first measurement value," and that measured by the second measurement value calculator 213 is referred to also as "second measurement value."

The first measurement value calculator 212 and the second measurement value calculator 213 may be configured to be able to measure only one of the blood refill time and the index related to the blood oxygen saturation.

The first measurement value calculator 212 and the second measurement value calculator 213 supply the first measurement value and the second measurement value to the outputting section 23.

The outputting section 23 outputs the first measurement value and the second measurement value. The output includes processes such as a display process in which the first measurement value and the second measurement value are displayed on a screen of a display disposed on the housing of the measuring apparatus 20, a print process in which the first measurement value and the second measurement value are printed on a print sheet, and a transmission process in which the first measurement value and the second measurement value are transmitted to another apparatus having a display.

Figure 3:
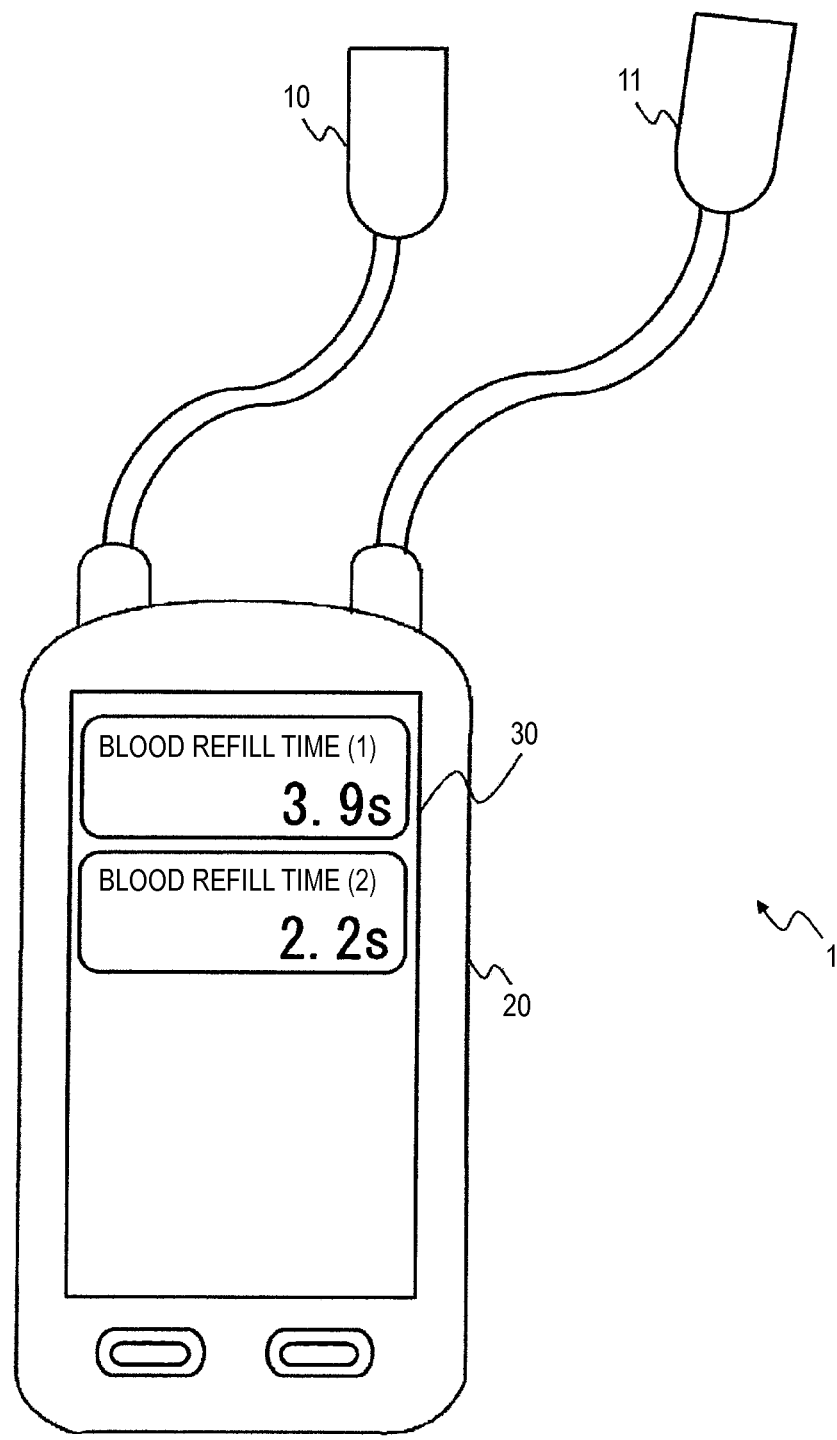
FIG. 3 is a conceptual view showing an example of an output screen which is produced by an outputting section 23 in Embodiment 1.

FIG. 3 is a conceptual view showing an example of an output screen which is produced by the outputting section 23. In the example of FIG. 3, a configuration is shown in which the first sensor 10 and the second sensor 11 are attached to the fingertips, respectively, and the housing has a display. A display screen 30 shows that the first measurement value (Blood refill time (1)) is 3.9 seconds, and the second measurement value (Blood refill time (2)) is 2.3 seconds. When referring to the display screen 30, the medical person can know that the peripheral circulation on the side of the first sensor 10 is poor.

The inputting section 22 is an input interface through which an input from the medical person is received. For example, the inputting section 22 is configured by buttons, knobs, and touch panel disposed on the measuring apparatus 20. The medical person inputs operations such as an operation of starting the measurement though the inputting section 22.

Then, effects of the measuring system 1 of the embodiment will be described. As described above, the pressure controller 211 starts the releases of the compressions applied to the first and second sensors 10, 11 at a substantially same timing. Therefore, the blood refillings in the first and second portions are started substantially at the same timing. Since the timings are the same, the difference in condition of the blood circulation between a plurality of portions is correctly reflected in the first and second measurement values. When referring to the first and second measurement values, the medical person can correctly determine the condition of the cardiovascular system of the subject.

In the case where (the first portion=the finger of the right hand, the second portion=the finger of the left hand), and the difference between the blood refill times is large, for example, the medical person can know that there is a possibility that arteriosclerosis obliterans (ASO) may occur in the hand in which the measurement value is larger. Similarly, in the case where (the first portion=the finger of the right hand, the second portion=the finger of the left hand), and the difference between the indexes related to the blood oxygen saturation after an elapse of a predetermined time period from the compression release is large, the medical person can know that there is a possibility that arteriosclerosis obliterans (ASO) may occur in the hand in which the measurement value is smaller.

In the case of (the first portion=the forehead, the second portion=the finger of the left hand (or the finger of the right hand)), the medical person can know also the conditions of the central and peripheral circulations of the subject.

Even in the case where the timings of starting the compression release in the first and second sensors 10, 11 are slightly different from each other (for example, about 0.1 second), when the difference between the timings is within a predetermined time period (for example, 0.3 seconds or shorter), the blood refilling in the both portions (first and second portions) are started at a substantially same timing. Therefore, the pressure controller 211 is required only to control the timing of starting the compression release in the first sensor 10, and that of starting the compression release in the second sensor 11 so that the difference between them is within the predetermined time period (preferably, started at a substantially same timing). Although the accuracy is lower, even when the compression release of the second sensor is performed within a short time period after ending of the measurement using the first sensor 10, it is possible to measure a desired value. Therefore, the above-described predetermined time period is about 0 to 0.3 seconds (preferably, 0 second), but has a concept including a value range of about 0 to 10 seconds.

<Embodiment 2>

Then, a measuring system 1 of Embodiment 2 of the invention will be described. The measuring system 1 of the embodiment is characterized in that the cardiovascular system of the subject is evaluated by using the first and second measurement values in the measuring apparatus 20. The configuration of the measuring system 1 of the embodiment which is different from that of Embodiment 1 will be described. In the following description, it is assumed that the processing sections which are identified by the same names and reference numerals as those of Embodiment 1 perform the processes identical with those of Embodiment 1 unless otherwise indicated.

Figure 4:
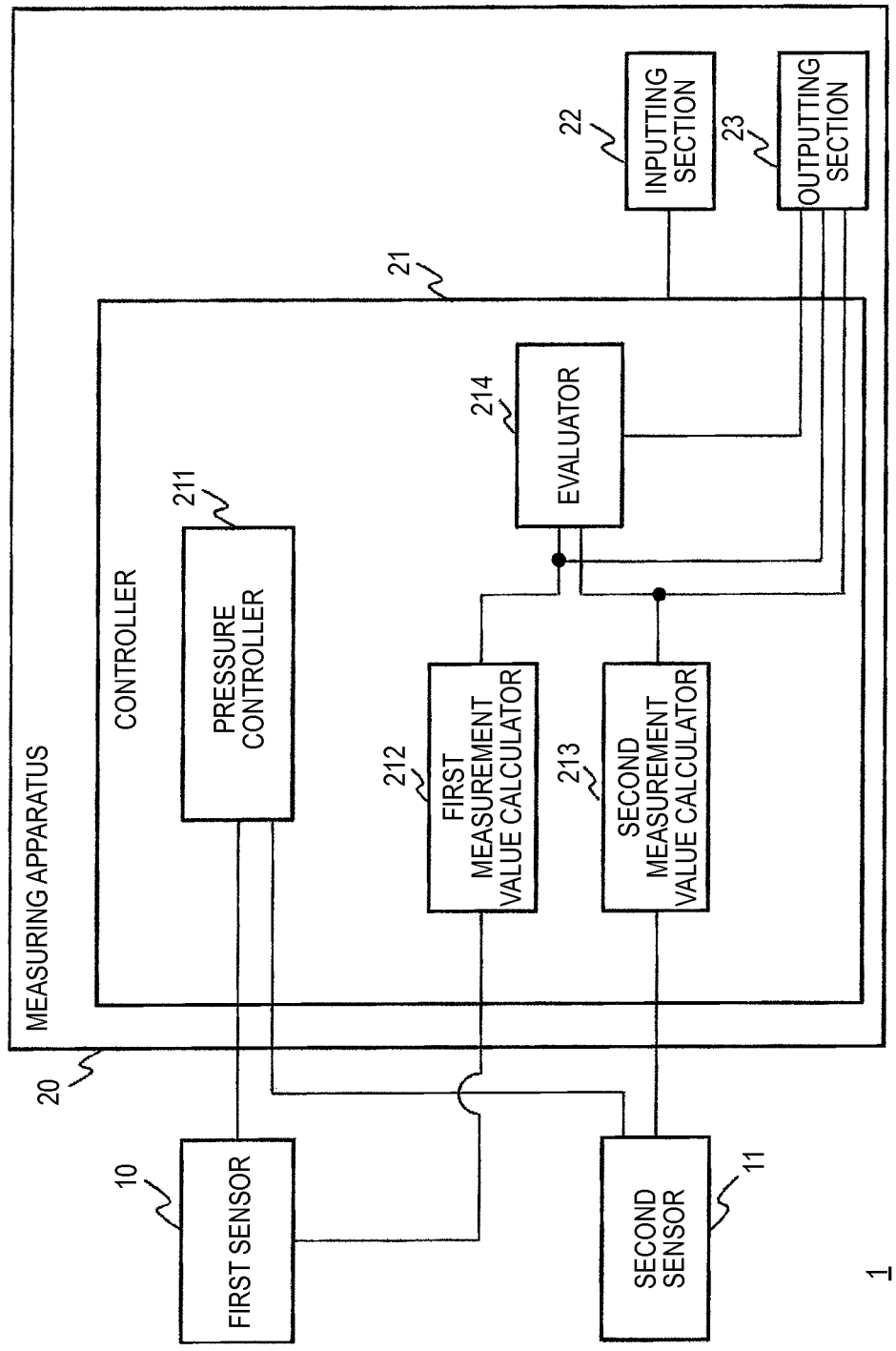
FIG. 4 is a block diagram showing a measuring system 1 of Embodiment 2.

FIG. 4 is a block diagram showing the configuration of the measuring system 1 of the embodiment. The measuring apparatus 20 in the measuring system 1 has an evaluator 214 in the controller 21 in addition to the configuration (FIG. 1) of Embodiment 1.

The evaluator 214 receives the first measurement value (the blood refill time or the index related to the blood oxygen saturation) from the first measurement value calculator 212, and the second measurement value (the blood refill time or the index related to the blood oxygen saturation) from the second measurement value calculator 213.

The evaluator 214 evaluates the cardiovascular system of the subject by using the first and second measurement values. Both the blood refill time and the index related to the blood oxygen saturation are indexes indicating whether the blood circulation to a body portion is good or not. As the first and second measurement values, therefore, the blood refill time can be used, or the index related to the blood oxygen saturation can be used. In the following description, it is assumed that the blood refill time is used as the first and second measurement values. The evaluation in the evaluator 214 will be described in detail.

(Evaluation Method 1)

In Evaluation method 1, evaluation is performed by using s comparison between the first measurement value and a threshold, and that between the second measurement value and the threshold. FIG. 5 shows an evaluation method performed by the evaluator 214 in the case of (the first portion=the fingertip, the second portion=the forehead).

A threshold Tth1 is determined based on a usual reference value (for example, 3 seconds) of the blood refill time. Alternatively, the medical person may set the threshold Tth1 by considering the age, sex, previous diseases, and the like of the subject. In the case where the first measurement value (blood refill time of the fingertip) is larger than the threshold Tth1, it is indicated that the circulation (peripheral circulation) of the blood to the fingertip is not good. In the case where the second measurement value (blood refill time of the forehead) is larger than the threshold Tth1, it is indicated that the circulation of the blood to the forehead is not good. Therefore, the evaluator 214 evaluates the cardiovascular system of the subject in the following manner (FIG. 5).

Case 1: the central circulation and the peripheral circulation are good,
Case 2: the central circulation is good, but the peripheral circulation is poor,
Case 3: the central circulation is good, but the blood flow to the head is reduced, and
Case 4: the central circulation and the peripheral circulation are poor (or the central circulation is very poor).

The evaluator 214 notifies the medical person of the evaluation result through the outputting section 23. In accordance with the notification, therefore, the medical person can perform an adequate procedure. In the case where only the peripheral blood flow is poor (Case 2), for example, it is considered that the skin temperature of the fingertip is low, or administration of a vasoconstrictor affects the blood flow. Therefore, the medical person can perform a procedure for improving the peripheral circulation.

FIG. 6 is a table showing the evaluation method performed by the evaluator 214 in the case of (the first portion=the fingertip of the left hand, the second portion=the fingertip of the right hand).

In the case where the first measurement value (blood refill time of the fingertip of the left hand) is larger than the threshold Tth1, it is indicated that the circulation (peripheral circulation) of the blood to the fingertip of the left hand is not good. In the case where the second measurement value (blood refill time of the fingertip of the right hand) is larger than the threshold Tth1, it is indicated that the circulation (peripheral circulation) of the blood to the fingertip of the right hand is not good. Therefore, the evaluator 214 evaluates the cardiovascular system of the subject in the following manner (FIG. 6).

Case 5: the peripheral circulations in the right and left hands are good,
Case 6: the peripheral circulation in the left hand is poor (suspicion of ASO),
Case 7: the peripheral circulation in the right hand is poor (suspicion of ASO), and
Case 8: the peripheral circulations in the right and left hands (or the central circulation) are poor.

As described above, in the case where both the first and second measurement values are smaller than the threshold, the evaluator 214 determines that the condition is normal, and, in another case, determines that any abnormality occurs. The evaluator 214 notifies the medical person of the evaluation result through the outputting section 23. In accordance with the notification, therefore, the medical person can perform an adequate procedure. In the case where peripheral circulation of the fingertip of only one of the hands is poor, for example, the medical person may perform diagnosis and treatment while assuming that the subject has a suspicion of arteriosclerosis obliterans (ASO).

The above is a summary of Evaluation method 1. Although, in the above description, it is assumed that the first and second measurement values are blood refill times, the evaluator 214 can perform evaluation by the strictly identical technique while using an index relating to the blood oxygen saturation. In the case where the information $\Delta Ab$ is used as an index relating to the blood oxygen saturation, the threshold Tth1 may be determined by using, for example, 0.1 as a reference. In the case where the blood oxygen saturation S is used, the threshold Tth1 may be determined, for example, to be about 10%.

(Evaluation Method 2)

Then, a second evaluation method will be described. In Evaluation method 2, evaluation is performed based on a comparison between the difference of the first and second measurement values, and a predetermined threshold. FIG. 7 shows an evaluation method performed by the evaluator 214 in the case of (the first portion=the fingertip, the second portion=the forehead).

In the case where the value (difference value) which is obtained by subtracting the second measurement value (the blood refill time in the forehead) from the first measurement value (the blood refill time in the fingertip) is larger than a threshold Tth2, it is indicated that the blood flow (peripheral circulation) in the fingertip is poorer than the blood flow (central circulation) to the forehead. In the case where the value (difference value) which is obtained by subtracting the first measurement value (the blood refill time in the fingertip) from the second measurement value (the blood refill time in the forehead) is larger than the threshold Tth2, it is indicated that no problem is detected in the peripheral circulation, but the blood flow in the forehead is poor. Therefore, the evaluator 214 evaluates the cardiovascular system of the subject in the following manner (FIG. 7).

Case 9: the peripheral circulation is poor,
Case 10: the blood flow to the forehead is poor, and
Case 11: there is no difference in blood circulation between the fingertip and the forehead.

In accordance with the evaluation by the evaluator 214, the medical person may perform an adequate procedure. Then, the evaluation method by the evaluator 214 in the case of (the first portion=the fingertip of the left hand, the second portion=the fingertip of the right hand) will be described (FIG. 8).

Case 12: the peripheral circulation in the left hand is poor (suspicion of ASO),
Case 13: the peripheral circulation in the right hand is poor (suspicion of ASO), and
Case 14: there is no difference in blood circulation between the right and left hands.

In the case where the difference between the blood refill times is large as shown in FIG. 8, the evaluator 214 evaluates that the subject has a suspicion of arteriosclerosis obliterans (ASO) or the like. In accordance with the evaluation by the evaluator 214, the medical person may perform an adequate procedure.

In FIGS. 7 and 8, the threshold Tth2 is used in both the comparison with (the first measurement value–the second measurement value), and that with (the second measurement value–the first measurement value). The comparison manner is not limited to this. A comparison process may be performed in which two thresholds, i.e., a threshold in the comparison with (the first measurement value–the second measurement value), and that in the comparison with (the second measurement value–the first measurement value) are used.

(Evaluation Method 3)

Then, a third evaluation method will be described. In Evaluation method 3, both the technique in Evaluation method 1 (the evaluation method in which the difference between the first measurement value and the threshold, and that between the second measurement value and the threshold are used), and that in Evaluation method 2 (the evaluation method in which the difference between the first measurement value and the second measurement value is used) are employed.

Hereinafter (FIG. 9), an evaluation method performed by the evaluator 214 in the case of (the first portion=the fingertip, the second portion=the forehead) will be described.

Case 15: approximately normal, but the fingertip (peripheral circulation) is somewhat poor,
Case 16: approximately normal, but the blood flow to the forehead is somewhat poor,
Case 17: the central circulation and the peripheral circulation are good,
Case 18: the case does not occur,
Case 19: the blood flow to the forehead is poor,
Case 20: both the fingertip (peripheral circulation) and the central circulation (forehead) are slightly poor (the both have values which are close to the threshold Tth1),
Case 21: the blood flow to the fingertip (peripheral circulation) is poor (suspicion of ASO),
Case 22: the case does not occur,
Case 23: both the fingertip (peripheral circulation) and the central circulation (forehead) are slightly poor (the both have values which are close to the threshold Tth1),
Case 24: both the central circulation and the peripheral circulation are poor, and particularly the blood flow to the fingertip (peripheral circulation) is poor,
Case 25: both the central circulation and the peripheral circulation are poor, and particularly the blood flow to the forehead is poor, and
Case 26: the central circulation is very poor.

As described above, the evaluator 214 evaluates the cardiovascular system of the subject based on the discrepancy between the blood refill times of the portions and the normal value, and comparisons between the blood refill times of the portions. When evaluation is performed based on the plurality of subtraction processes as described above, the evaluator 214 can perform evaluation which is more correct. In the above-described evaluations using Tables 1, 3, and 5 above, it is assumed that the second measurement value is acquired from the vicinity of the forehead. Alternatively, the second measurement value may be acquired from the nose or the earlobe. Namely, the second measurement value is required to be acquired from the vicinity of the head of the subject.

Then, the evaluation method performed by the evaluator 214 in the case of (the first portion=the fingertip of the left hand, the second portion=the fingertip of the right hand) will be described (FIG. 10).

Case 27: approximately normal, but the fingertip of the left hand (peripheral circulation of the left hand) is somewhat poor,
Case 28: approximately normal, but the fingertip of the right hand (peripheral circulation of the right hand) is somewhat poor,
Case 29: there is no difference between the right and left hands, and the peripheral circulation and the central circulation are good,
Case 30: the case does not occur,
Case 31: peripheral circulation of the right hand is poor (suspicion of ASO),
Case 32: one or both of the peripheral circulation and the central circulation are slightly poor (the both have values which are close to the threshold Tth1),
Case 33: peripheral circulation of the left hand is poor (suspicion of ASO),
Case 34: the case does not occur,
Case 35: one or both of the peripheral circulation and the central circulation are slightly poor (the both have values which are close to the threshold Tth1),
Case 36: one or both of the peripheral circulation and the central circulation are slightly poor, and particularly the peripheral circulation of the left hand is poor,
Case 37: one or both of the peripheral circulation and the central circulation are slightly poor, and particularly the peripheral circulation of the right hand is poor, and
Case 38: one or both of the peripheral circulation and the central circulation are poor.

The evaluator 214 evaluates the cardiovascular system of the subject as described above. In the case where both the first and second measurement values are large (Case 38), the evaluator 214 cannot determine whether the peripheral circulations of the both hands are poor, or the central circulation is poor. In such a case, evaluation in which a blood refill time that is measured by a third sensor attached to the forehead or the like is considered may be performed.

In the above description, the first and second measurement values are compared with the threshold Tth1. Alternatively, thresholds may be set respectively for measurement values. The threshold which is to be compared with (the first measurement value−the second measurement value) may be different from that which is to be compared with (the second measurement value−the first measurement value) (two thresholds may be set in place of the threshold Tth2).

Although the examples of the evaluation technique performed by the evaluator 214 have been described, the evaluator 214 may evaluate the cardiovascular system of the subject by using another technique as far as, in the technique, evaluation using the first and second measurement values is performed. The evaluation performed by the evaluator 214 includes not only the above-described determination of normal/abnormal, but also a simple subtraction process in which the differences between the first measurement value and the threshold, and between the second measurement value and the threshold are calculated. A configuration may be employed in which the difference values (differences between the first measurement value and the threshold, and between the second measurement value and the threshold) calculated by the evaluator 214 are output through the outputting section 23 (a display, printing, writing into a file, or the like). Similarly, the evaluation performed by the evaluator 214 includes also a simple subtraction process in which the difference between the first measurement value and the second measurement value is calculated. The difference value (difference value between the first measurement and the second measurement value) calculated by the evaluator 214 may be output through the outputting section 23 (a display, printing, writing into a file, or the like).

Figure 11:
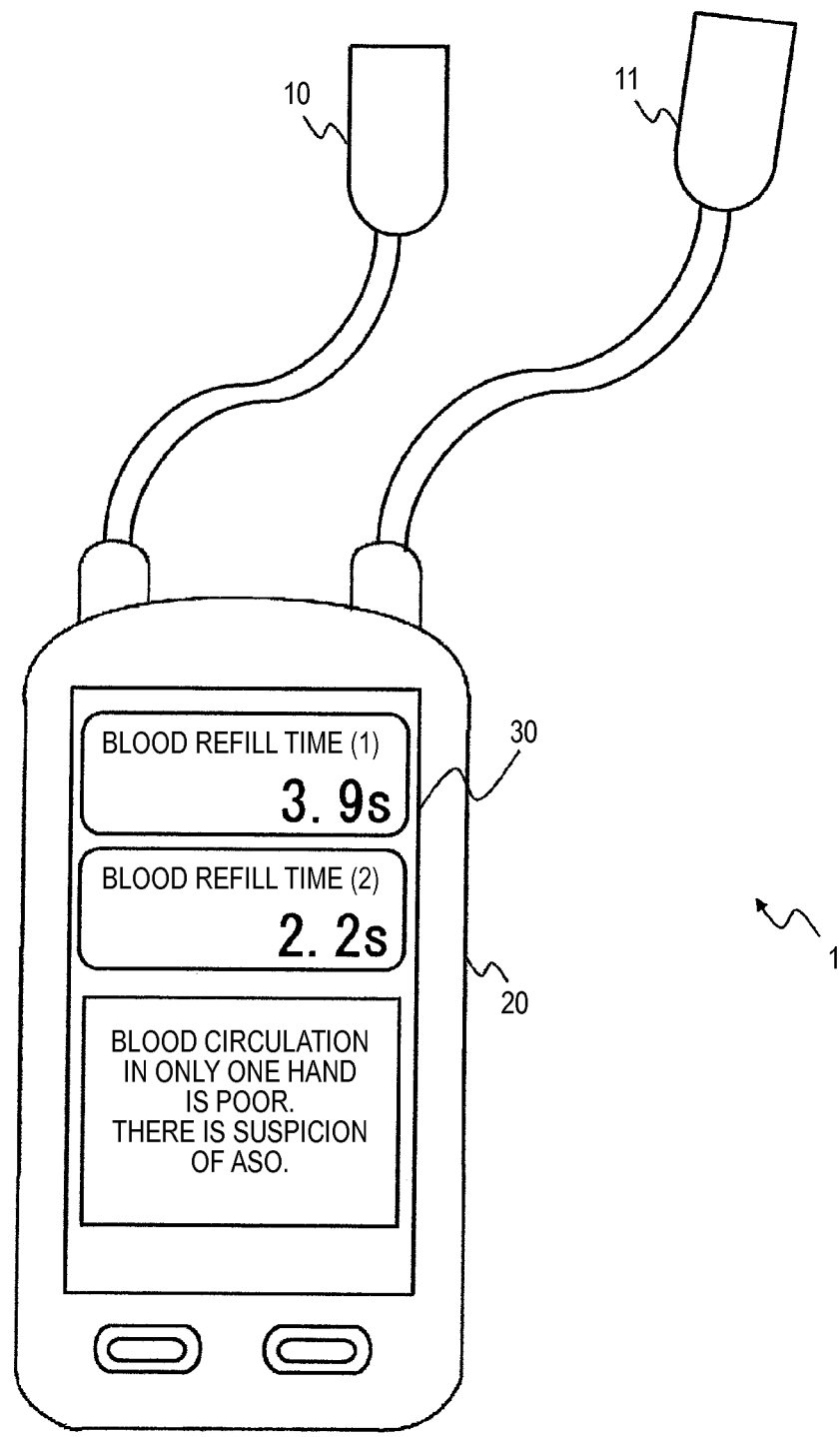
FIG. 11 is a conceptual view showing an example of an output screen which is produced by an outputting section 23 in Embodiment 2.

Next, an example of the display performed by the outputting section 23 will be described. FIG. 11 is a conceptual view showing a display screen which displays a result of evaluation by the evaluator 214. The display screen 30 shows that the first measurement value (Blood refill time (1)) is 3.9 seconds, and the second measurement value (Blood refill time (2)) is 2.3 seconds. The display screen 30 further shows a result of evaluation by the evaluator 214. In the example of FIG. 11, it is shown that the subject has a suspicion of arteriosclerosis obliterans (ASO). When referring to the display screen 30, the medical person can recognize the result of evaluation of the cardiovascular system of the subject.

The outputting section 23 may be configured so as to, in accordance with the result of the evaluation by the evaluator 214, perform not only the production of the display screen 30, but also an output of an alarm sound. That is, the outputting section 23 may have a configuration where, when the evaluator 214 determines that the subject has an abnormality of the cardiovascular system, and alarm sound is output.

Then, effects of the measuring system 1 of the embodiment will be described. The measuring system 1 of the embodiment has the configuration where the cardiovascular system of the subject is evaluated by using measurement values (first and second measurement values) related to the blood circulations in a plurality of portions. Even if the medical person is inexperienced in diagnosing the cardiovascular system, when the measuring system 1 evaluates the cardiovascular system, the medical person can correctly know the condition of the cardiovascular system of the subject.

In above-described Evaluation method 1, evaluation is performed based on the threshold which is determined on the basis of the normal value of the blood refill time (or an index related to the blood oxygen saturation). Therefore, the medical person can know evaluation based on whether the blood circulations of portions are normal or not.

In above-described Evaluation method 2, evaluation is performed based on whether the difference between the first measurement value and the second measurement value is equal to or larger than the predetermined threshold of not. Therefore, the medical person can know a result of evaluation in which partial impairment of the blood circulation (for example, ASO) or the like is correctly detected.

In above-described Evaluation method 3, both the techniques of Evaluation method 1 (the evaluation method using the differences between the first measurement value and the threshold, and between the second measurement value and the threshold) and Evaluation method 2 (the evaluation method using the difference between the first measurement value and the second measurement value) are used. That is, the evaluator 214 performs evaluation based on whether the first measurement value and the second measurement value are normal values or not, and whether the difference between the first measurement value and the second measurement value is excessively large or not. Therefore, the medical person can know more correctly the conditions of the blood circulations of portions and the condition of the difference between the right and left hands.

The outputting section 23 outputs (preferably, displays) the evaluation result by the evaluator 214 in addition to the first and second measurement values. Even if the medical person is less experienced, therefore, the medical person can adequately know the condition of the cardiovascular system of the subject.

Although the invention conducted by the inventors has been specifically described based on the embodiments, the invention is not limited to the above-described embodiments, and it is a matter of course that various changes can be made without departing from the spirit of the invention.

As described above, the measuring system 1 may be configured so that three or more sensors are attached to the subject, and evaluation is performed by using three or more measured blood refill times (or indexes related to the blood oxygen saturation).

Figure 12:
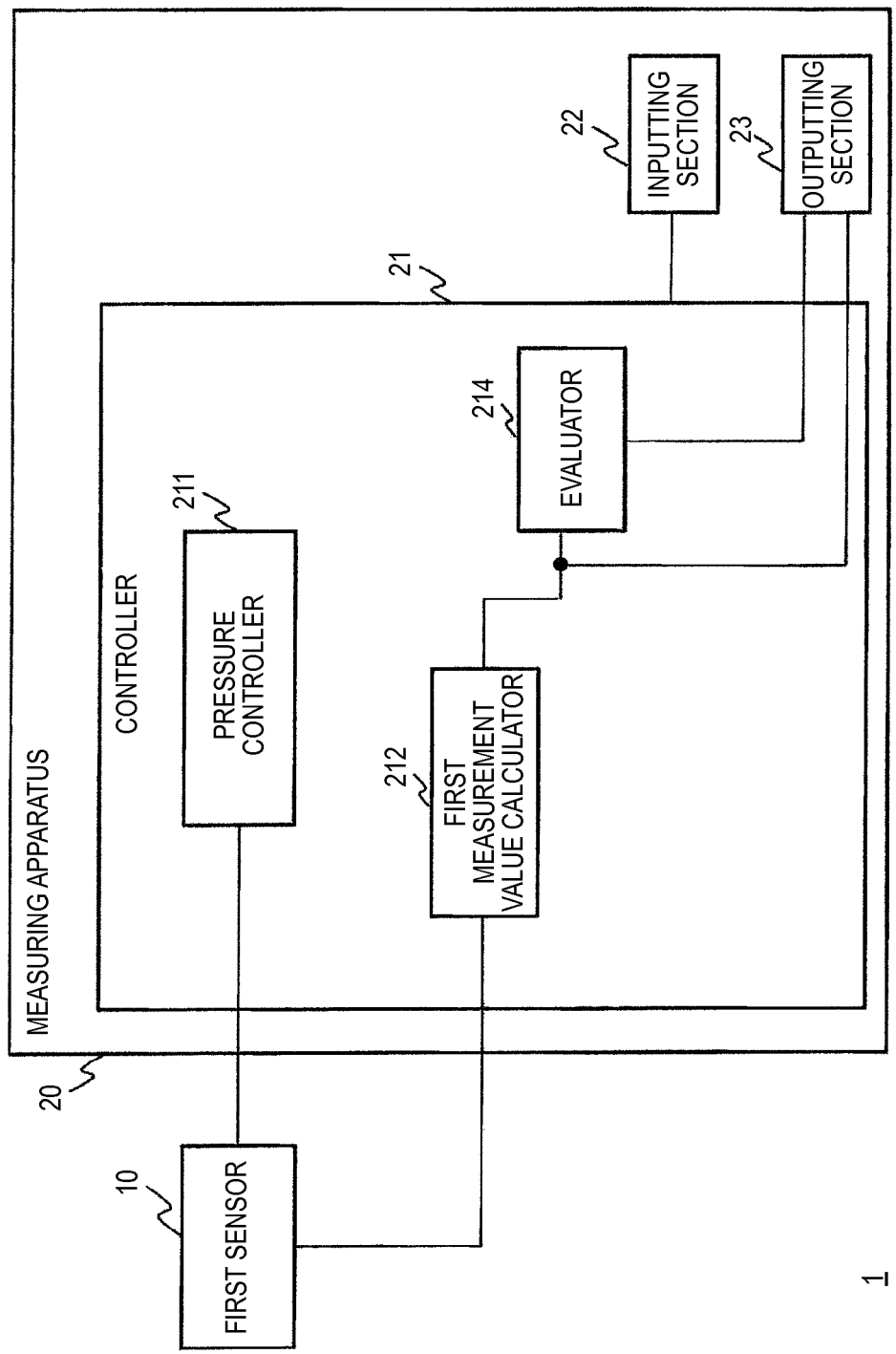
FIG. 12 is a block diagram showing the configuration of the measuring system 1 of Embodiment 1.

Alternatively, the measuring system 1 may have only one sensor, and the first and second portions may be sequentially measured by using the sensor (the configuration of FIG. 12). Namely, the first measurement value (blood refill time or index related to the blood oxygen saturation) is calculated from the first portion (the first calculation step), and thereafter the second measurement value (blood refill time or index related to the blood oxygen saturation) is calculated from the second portion (the second calculation step). While using the first and second measurement values, thereafter, the cardiovascular system of the subject may be evaluated by using the above-described techniques (the evaluation step). Also in the alternative, evaluation is performed by using measurement values related to the blood circulations of a plurality of portions, and therefore the cardiovascular system of the subject can be adequately evaluated.

What is claimed is:

1. A measuring system comprising:
   a first sensor configured to emit light to a first portion of a subject, to compress the first portion, and to measure reflected light or transmitted light from the first portion;
   a second sensor configured to emit light to a second portion of the subject, to compress the second portion, and to measure reflected light or transmitted light from the second portion;
   a first measurement value calculator configured to calculate, based on a change of an amount of received light that is measured by the first sensor, a first measurement value indicating a first blood refill time;
   a second measurement value calculator configured to calculate, based on a change of an amount of received light that is measured by the second sensor, a second measurement value indicating a second blood refill time; and
   a pressure controller configured to control the first sensor and the second sensor so that a time difference between a start of compression release by the first sensor and a start of compression release by the second sensor is within a predetermined time period.

2. The measuring system according to claim 1, wherein the pressure controller is further configured to control a first time period from the start of compression release by the first sensor to an end of compression, and a second time period from the start of compression release by the second sensor to an end of compression so that the first time period and the second time period are substantially equal to each other.

3. The measuring system according to claim 1 further comprising an evaluator configured to evaluate a cardiovascular system of the subject based on a comparison process using the first measurement value and the second measurement value.

4. The measuring system according to claim 3, wherein the evaluator is further configured to calculate:
   a difference value between the first measurement value and a threshold, and a difference value between the second measurement value and a threshold; or
   a difference value between the first measurement value and the second measurement value.

5. The measuring system according to claim 3, wherein the evaluator is further configured to calculate a first difference value between the first measurement value and a threshold, to calculate a second difference value between the second measurement value and the threshold, and to evaluate the cardiovascular system of the subject based on the first difference value and the second difference value.

6. The measuring system according to claim 5, wherein, in a case where both the first measurement value and the second measurement are smaller than the threshold, the evaluator is further configured to determine that the cardiovascular system of the subject is normal, and, in the other case, the evaluator is further configured to determine that the cardiovascular system of the subject is abnormal.

7. The measuring system according to claim 3, wherein the evaluator is further configured to calculate a difference value between the first measurement value and the second measurement value, and, in a case where the difference value is larger than a threshold, is further configured to determine that the cardiovascular system of the subject is abnormal.

8. The measuring system according to claim 3, wherein the evaluator is further configured to evaluate the cardiovascular system of the subject based on a comparison between the first measurement value and a predetermined threshold, a comparison between the second measurement value and a predetermined threshold, and a difference between the first measurement value and the second measurement value.

9. The measuring system according to claim 3 further comprising an outputting section configured to display the first measurement value, the second measurement value, and a result of evaluation by the evaluator on a same screen.

10. The measuring system according to claim 9, wherein the outputting section is further configured to output an alarm sound when the evaluator determines that the cardiovascular system of the subject is abnormal.

11. The measuring system according to claim 1 further comprising an outputting section configured to output the first measurement value and the second measurement value.

12. The measuring system according to claim 1, wherein the first portion is a fingertip of one hand of the subject, and the second portion is a fingertip of another hand of the subject.

13. The measuring system according to claim 1, wherein the first portion is a fingertip of one hand of the subject, and the second portion is a vicinity of a head of the subject.

14. The measuring system according to claim 1, wherein the predetermined time period is a range from 0 to 10 seconds.

15. A measuring apparatus including:
   a first measurement value calculator configured to calculate, based on a change of an amount of received light that is measured by a first sensor, a first blood refill time, the first sensor being configured to emit light to, receive light from, and compress a first portion of a subject;
   a second measurement value calculator configured to calculate, based on a change of an amount of received light that is measured by a second sensor, a second blood refill time, the second sensor being configured to emit light to, receive light from, and compress a second portion of the subject; and
   a pressure controller configured to control the first sensor and the second sensor so that a time difference between a start of compression release by the first sensor and a start of compression release by the second sensor is within a predetermined time period.

16. A measuring apparatus comprising:
   a first measurement value calculator configured to calculate a first blood refill time by emitting light to a first portion of a subject and based on a change of an amount of reflected light or transmitted light from the first portion after releasing compression of the first portion;
   a second measurement value calculator configured to calculate a second blood refill time by emitting light to a second portion of the subject and based on a change of an amount of reflected light or transmitted light from the second portion after releasing compression of the second portion; and
   an evaluator configured to evaluate a cardiovascular system of the subject based on a comparison process using the first blood refill time and the second blood refill time.

17. The measuring apparatus according to claim 16, wherein the evaluator is further configured to evaluate the cardiovascular system of the subject based on a comparison between the first blood refill time and a first predetermined threshold, and a comparison between the second blood refill time and a second predetermined threshold.

18. The measuring apparatus according to claim 16, wherein the evaluator is further configured to calculate a difference value between the first blood refill time and the second blood refill time, and to evaluate the cardiovascular system of the subject based on a comparison between the difference value and a threshold.

19. The measuring apparatus according to claim 16, wherein the evaluator is further configured to evaluate a peripheral circulation and a central circulation of the subject, or a difference of the peripheral circulation between right and left, based on a comparison between the first blood refill time and a first predetermined threshold, a comparison between the second blood refill time and a second predetermined threshold, and a difference between the first blood refill time and the second blood refill time.

20. The measuring apparatus according to claim 16, wherein:
   the first measurement value calculator is further configured to calculate a first index related to a bold oxygen saturation by emitting light to the first portion of the subject and based on a change of an amount of reflected light or transmitted light from the first portion after releasing compression of the first portion,
   the second measurement value calculator is further configured to calculate a second index related to a bold oxygen saturation by emitting light to the second portion of the subject and based on a change of an amount of reflected light or transmitted light from the second portion after releasing compression of the second portion,
   the evaluator is further configured to evaluate the cardiovascular system of the subject based on a comparison process using the first index and the second index.

* * * * *